Figure 1:
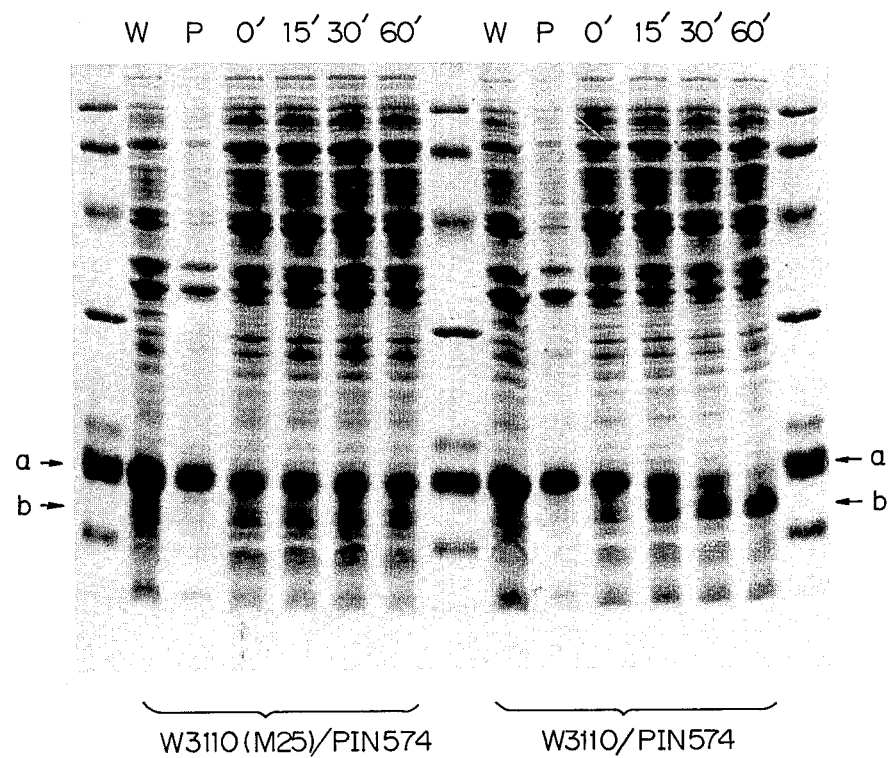

United States Patent [19]

Sugimura et al.

[11] Patent Number: 4,874,697

[45] Date of Patent: Oct. 17, 1989

[54] HOST *E. COLI* AND USE THEREOF

[75] Inventors: Keijiro Sugimura; Shunjiro Sugimoto; Hounai Shirasawa, all of Osaka, Japan

[73] Assignee: Suntory Limited, Osaka, Japan

[21] Appl. No.: 947,398

[22] Filed: Dec. 29, 1986

[30] Foreign Application Priority Data

Dec. 27, 1985 [JP] Japan .................................. 60-295140

[51] Int. Cl.$^4$ ....................... C12P 21/00; C12R 1/185
[52] U.S. Cl. .................................. 435/68; 435/172.1; 435/172.3; 435/252.33; 435/252.8; 424/85.5
[58] Field of Search ....................... 435/68, 172.3, 253, 435/252.33, 252.8, 172.1, 70

[56] References Cited

U.S. PATENT DOCUMENTS 4,590,159 5/1986 Markovitz et al. .................... 435/68
4,758,512 7/1988 Goldberg et al. ................. 435/172.1

FOREIGN PATENT DOCUMENTS

WO8503949 9/1985 European Pat. Off. .

OTHER PUBLICATIONS

J. Grodberg, et al., Nucleic Acids Research, vol. 16, No. 3, 1988, p. 1209.
Sugimura and Nishihara, Journal of Bacteriology, Dec. 1988, vol. 170, No. 12.
K. R. Rupprecht, et al., Journal of Bacteriology, Feb. 1983, pp. 1104–1106, vol. 153, No. 2.
E. H. Fiss, et al., Biochemical and Biophysical Research Communications, vol. 91, No. 1, Nov. 14, 1979, pp. 29–34.
Gayda and Markovitz, Journal of Bacteriology, Oct. 1978, pp. 369–389, vol. 136, No. 1.
G. Gordon, et al., Mol. Gen. Genet. (1984) 193:414–421.
Nature New Biolog, vol. 234, Nov. 10, 1971, pp. 51–52.
Patent Abstracts of Japan, vol. 8, No. 273 (C256)(1710), Dec. 13, 1984.
Chemical Abstracts, vol. 103, Abstract No. 117179b, 1985.
Susan Gottesman et al., Journal of Bacteriology, vol. 138, No. 1 (1981) pp. 265–273.
Carol Heiman et al., Journal of Bacteriology, vol. 135, No. 2 (1978) pp. 588–594.

*Primary Examiner*—Blondel Hazel
*Attorney, Agent, or Firm*—Cushman, Darby & Cushman

[57] ABSTRACT

*E. coli* deficient in protease activities, said activities being not inhibited with diisopropyl fluorophosphate, phenylmethylsulfonyl fluoride, N-α-tosyl-L-lysyl chloromethyl ketone, N-tosyl-L-phenylalanine chloromethyl ketone, ethylenediamine tetra-acetic acid, leupeptin, antipain, $\alpha_2$-macroglobulin or chymostatin, and being inhibited with zinc chloride or copper chloride is disclosed.

This *E. coli* is useful as a host for creating a transformant capable of expressing an exogenous protein or polypeptide.

The protein or polypeptide expressed by the transformant may be extracted and purified with a quite low level of decomposition.

5 Claims, 1 Drawing Sheet

HOST E. COLI AND USED THEREOF

This invention relates to a novel strain of *Escherichia coli* (*E. coli*) useful as a host cell for a vector capable of expressing an exogenous protein or polypeptide in high yield. This invention also relates to a method for producing a protein or polypeptide in a high yield from a transformant of the novel *E. coli* which is used as a host.

More particularly, this invention relates to a novel strain of *E. coli* deficient in activity for decomposing human immune interferon (referred to as "h-IFN-γ hereunder) and to a method for efficiently producing a protein or polypeptide having h-IFN-γ activity.

It has recently become possible, thanks to the progress in genetic engineering, to produce many physiologically active proteins and polypeptides (proteins and polypeptides are merely referred to as "protein" hereunder for the purpose of simplifying the description) in large amounts from microorganisms, although these substances have been produced by separation and purification from an organism which produces them in a very small amount. Accordingly, although their presence had previously been confirmed only by their activities, it has now become possible to use these physiologically active proteins and polypeptides as active ingredients in drugs and agricalatural preparations.

Many improvements of the recombinant techniques have been proposed mainly from the viewpoint of ensuring efficient production of the desired substances. For example, there have been improvements in vectors, development of novel host-vector systems, and improvements in culture medium or cultivation conditions. In addition, proteins having stable amino acid sequences have been developed by the use of so-called protein engineering techniques.

However, although pharmacologically active proteins are expressed in high yields in a transformant, too many steps have been required for extracting and purifying the proteins. It goes without saying that the establishment of a method for easy and efficient extraction and purification of a protein from a tranformant capable of producing the protein is important and useful from the viewpoint of industry.

Usually, in extracting and purifying a protein obtained from recombinant microorganisms (transformants), cultured microorganisms are first killed by using a bactericide (if the extraction is conducted in a completely closed system, the killing step may be omitted). The dead cells are then disrupted, the suspension of disrupted cells centrifugated and either the supernatant or the precipitate subjected to a purification step. Howver, during these treatment steps, the desired protein is sometimes decomposed because of the strong protease activity in the extract of the supernatant and the precipitate.

For example, in one case of h-IFN-γ production using E. coli as a host cell, during extraction after disruption of the cells, a high proportion of a peptide having 131 amino acids is obtained which is derived by the decomposition (deletion) of the C-terminal region of the desired peptide which has 146 amino acids. In order to obtain the peptide having 146 amino acids, U.S. Pat. No. 4,476,069 proposed that a protease inhibitor be used to prevent the polypeptide from being digested, and Japanese Patent Public Disclosure No. 59-161321 disclosed a method wherein cellular proteins including the desired protein are aggregated and precipitated by the use of a protein denaturation agent simultaneous with the disruption of the cells. In addition, a copending application which has been assigned to the same company as this case, disclosed that a method for the efficient extraction and purification of h-IFN-γ using a combination of a copper or zinc salt with polyethyleneimine had been developed.

Additionally, some trials for simplifying the extraction of the 146 amino acid h-INF- have been made. In these trials, the desired protein was extra-cellularly produced by the transformants in a periplasmic space or culture medium thereby reducing the proportion of impurities in the culture medium or preventing, as much as possible, the digestion of the desired protein by the action of proteases. Although these trials have been conducted, such methods have not proved to be practical for actual use because of unsolved problems with respect to the desired secretion level of the protein, and the precision processing of precursor protein during the secretion process. The precursor protein is usually subject to a certain decomposition step wherein the desired protein is secreted.

The inventors have studied ways of solving the problems whereby h-INF-γ which is expressed in *E. coli* cells is easily decomposed, especially during extraction from the cultured cells. The inventors have found that such problems can be solved by using E. coli deficient in the activity of a certain kind of protease as host bacteria. On the basis of these findings, they completed this invention.

The intended mutant strains of *E. coli* which can be used as a host in this invention are those deficient in protease activities which are not inhibited by diisopropyl fluorophosphate, phenylmethylsulfonyl fluoride, N-α-tosyl-L-lysyl chloromethyl ketone, N-tosyl-L-phenylalanine chloromethyl ketone, ethylenediaminetetra-acetic acid (EDTA), leupeptin, antipain, α$_2$-macroglobulin or chymostatin, and which are inhibited by zinc chloride or copper chloride. More preferably, *E. coli* deficient in protease activity capable of decomposing polypeptide having human immune inferferon are used.

FIG. 1 is a photograph of SDS-PAGE showing the change with passage of time in decomposition levels of h-IFN-γ. In the photograph, W shows an SDS-PAGE pattern of the suspension of cultured cells before disruption, P represents the precipitate obtained by disrupting and centrifuging the suspension, and 0', 15', 30'and 60' represent the supernatant obtained by centrifugation after disruption of the cell suspension and after being incubated at 37° C. for 0, 15, 30 and 60 minutes, respectively. An arrow (a) indicates a band corresponding to h-IFN-γ protein. An arrow (b) shows a band corresponding to a partially decomposed h-IFN-γ.

The mutant strain of this invention can be obtained in the following manner.

*E. coli*, from which an intended host for a recombinant microorganism is to be obtained, is subjected to mutation inducing treatment. From the thus treated *E. coli* cells, the mutated strain deficient in activities capable of decomposing a desired protein such as h-IFN-γ is selected in, for example, the following manner.

The *E. coli* cells which have been subjected to mutation inducing treatment are cultivated, and after addition of the desired protein to the lysate of the cultivated cells, the lysate is subjected to SDS-polyacrylamide gel electrophoresis (abbreviated as "SDS-PAGE" hereunder) to detect the decomposition level of the added protein. If the *E. coli* to be analyzed is a transformant which can produce the desired protein in high yield, the desired mutant can be selected by directly subjecting a lysate or a culture solution of the transformant to SDS-PAGE.

The thus obtained mutant may be used as a host cell for producing a desired protein such as h-IFN-γ. The mutant is transformed by introducing therein a vector capable of expressing the desired protein, and the cells cultivated to produce the protein. The cultivated cells are collected and disrupted and the desired protein is isolated and purified therefrom. According to this invention, the desired protein can be recovered, without decomposition, even if no protease inhibitor or protein denaturating agent is used during the extraction step, because the host cell of the transformant is deficient in activities capable of decomposing the desired protein.

This invention will be illustrated in detail hereunder with respect to E. coli deficient in any activity capable of decomposing h-IFN-γ and to a transformant containing a vector capable of expressing h-IFN-γ. However, it should be understood that this invention is not to be construed as being limited to such *E. coli*. It is a matter of course that any *E. coli* deficient in a protease as explained above can be used in this invention.

Incidentally, the novel *E. coli* strain obtained according to this invention has been named SBM282 and deposited under the conditions of the Budapest Treaty at the Fermentation Research Institute, Japan under Serial No. FERM BP-1097.

EXAMPLE 1

Separation of a strain deficient in protease activities:

*E. coli* W3110(M25)/pIN5T4 capable of producing h-IFN-γ, namely, *E. coli* transformed with a plasmid pIN5T4 in which a tetracycline-resistant gene (Tc$^r$) was substituted for an ampicillin-resistant gene (Ap$^r$) in the plasmid pIN5GIF54 disclosed in Japanese Patent Public Disclosure No. 60-24187, was cultured at 37° C. overnight in an LB medium (0.5% yeast extract, 1% bacto-tryptone, 0.5% NaCl, pH 7.0). The cultured cells were collected by centrifugation at 10,000 rpm for 5 minutes, and eashed with an M9 medium (2 ml/l of 1 M MgSO$_4$, 10 ml/l of 20% glucose and 0.1 ml/l of CaCl$_2$ were added to a solution composed of 0.1% NH$_4$Cl, 0.6% Na$_2$HOP$_4$, 0.3% KH$_2$PO$_4$ and 0.05% NaCl, and adjusted to pH 7.4), and suspended in the same medium. To the suspension, nitrosoguanidine (abbreviated as NTG hereunder) as a mutation-inducing agent was added in an amount sufficient to achieve a final concentration of 50 μg/ml, followed by allowing it to stand for 30 minutes. The cells were then collected by centrifugation at 10,000 rpm for 5 minutes, and an LB medium was inoculated with the collected cells after they had been washed with the same medium. The cells were cultured on a plate at 37° C. overnight, and colonies growing on the plate were used to inoculate tubes containing 500 μl of an LB medium (one loop of colonies per tube), and cultured at 37° C. overnight. The cultured cells were collected by centrifugation at 10,000 rpm for 5 minutes and, after addition of 200 μl of Lysozyme-EDTA solution (500 μg/ml Lysozyme and 1 mM EDTA), disrupted by the freezing-thawing method. One hundred μl of h-IFN-γ solution at a concentration of 1 mg/ml was added to the disrupted cell suspension, and the mixture was incubated at 37° C. for one hour. To the mixture was added 150 μl of an SDS sample solution (10% glycerin, 5% of 2-mercaptoethanol, 23% SDS, 62.5 mM of Tris-HCL buffer, pH 6.8), and the mixture was then allowed to stand at 100° C. for 5 minutes. The mixture was centrifugated at 10,000 rpm for 10 minutes. and the supernatant was subjected to SDS-PAGE to determine the residual amount of h-IFN-γ having a molecular weight of about 18,000 and composed of 146 amino acids. Using this procedure, one strain deficient in activities for decomposing h-IFN-γ was selected from about 2,000 strains.

In order to confirm that this mutation of the proteolytic deficiency was not inherent in the plasmid but in the host cell, curing of the plasmid (pIN5T4) was conducted. That is, the selected mutant which exhibited tetracyclineresistance based on a gene on the plasmid (pIN5T4) was cultured in a medium free from tetracycline and a strain sensitive to tetracycline (Tc$^s$) was selected to confirm the deletion of the plasmid from the strain. The strain was treated as explained above by adding h-IFN-γ protein to the disrupted cell suspension of the strain, and the decomposition of the protein was analyzed by SDS-PAGE to confirm that no decomposition could be observed. These results showed that the mutant selected by this invention relied on the chromosomal mutation of the host strain.

The plasmid deleted strain was then transformed in the standardized manner with pIN5T4, the plasmid containing a gene capable of expressing h-IFN-γ. The transformant was selected using its tetracycline-resistance as a marker. The selected transformant was treated as explained above and the decomposition of h-IFN-γ in an extract of the lysate thereof was analyzed to confirm that no decomposition of h-IFN-γ had occurred.

The cured mutant W3110(M25) was named SBM282 and has been deposited under the conditions of the Budapest Treaty at the Fermentation Research Institute, Japan, under FERM BP-1097.

In addition to the above method, it is also possible to create and select a mutant by first treating with a mutation inducing agent *E. coli* in which no vector capable of expressing a desired protein has been introduced, and then selecting the intended strain of the treated *E. coli*. The desired vector can be introduced in the mutant. 2. Characteristics of the mutant obtained by treatment of a mutation inducing agent:

The strain deficient in h-IFN-γ decomposing activity which was obtained in Example 1 by treatment with a mutation inducing agent was studied for deficiency in proteolytic activities. The studies showed that the strain was deficient in proteolytic activities of the sort that are not inhibited by the use of an inhibitor of trypsin-like proteases, and that are inhibited by a salt of copper or zinc.

A transformant (W3110/pIN5T4) of the sort which is capable of expressing h-IFN-γ was also obtained using a strain of *E. coli* (W3110) which had not been treated with a mutation inducing agent and which was cultured at 37° C. overnight in 100 ml of LB medium in a 500 ml meyer flask. Then the cultured cells were collected by centrifugation at 8,000 rpm for 10 minutes. The wet cells (1 g) obtained were suspended in 30 ml of a 50 mM Tris-HCl buffer (pH 7.5) and homogenized with a French-press homogenizer at 20,000 psi followed by centrifugation at 8,000 rpm for 20 minutes.

The supernatant (50 μl per sample) was added to 700 μl of 0.1 M Tris-HCl buffer (pH, 7.5) containing a different protease inhibitor in the amount indicated in Table 1. A solution of h-IFN-γ(1 mg/ml) (250 μl) was added to the inhibitor-containing solution and the test solution was incubated at 37° C. for one hour. The solution was subjected to SDS-PAGE to detect the decomposition of h-IFN-γ.

The results are shown in Table 1.

TABLE 1

Inhibition effect of various inhibitors on h-IFN-γ decomposition

| Inhibitor | Concentration | *Level of h-IFN-γ decomposition | **Inhibition of h-IFN-γ decomposition |
|---|---|---|---|
| Control (no inhibitor) | — | ++ | — |
| Diisopropyl fluorophosphate | 0.1–10 mM | ++ | — |
| Phenylmethylsulfonyl fluoride | 0.1–1.0 mM | ++ | — |
| " | 10 mM | ++ | — |
| N—α-tosyl-L-lysyl chloromethyl keton | 0.1–1.0 mM | ++ | — |
| N—tosyl-phenylalanine chloromethyl ketone | 0.1–1.0 mM | ++ | — |
| EDTA | 0.1–10.0 mM | ++ | — |
| Leupeptin | 10–40 μg/ml | ++ | — |
| Antipain | 10–40 μg/ml | ++ | — |
| α$_2$-macroglobulin | 0.1–1.0 mg/ml | ++ | — |
| Chymostatin | 10–40 μg/ml | ++ | — |
| ZuCl$_2$ | 0.1–1 mM | — | + |
| CuCl$_2$ | 0.1–1 mM | — | + |

*+ or ++ represents occurrence of decomposition
**+ represents the positive inhibition effect As shown in Table 1, only CuCl$_2$ and ZnCl$_2$ exhibited the ability to inhibit the activity of h-IFN-γ decomposition. In contrast, the other inhibitors which are generally considered to be inhibitors for trypsin-like proteases did not exhibit h-IFN-γ decomposing activity. 3. Change with passae of time in h-IFN-γ decomposition after cell disruption:

The yield of h-IFN-γ production and change with passage of time in h-IFN-γ decomposition after disruption of the cultured cells was studied with respect to a transformant (W3110/pIN5T4) which was created using a wild-type strain as a host, and to a transformant [W3110(M25)/pIN5T4], the host of which was the mutant obtained according to this invention.

W3110/pIN5T4 and W3110(M25)/pIN5T4 were cultured, and the cells were collected and suspended in the buffer as described above. The suspension (W) and precipitate (P) prepared by disrupting the cells in the suspension with a French-press and centrifugating the disrupted cells, and the supernatants obtained by centrifugation and standing for 0, 15, 30 and 60 minutes were used as samples to determine by SDS-PAGE the amounts of non-decomposed h-IFN-γ(molecular weight, about 18,000) and decomposed protein (m.w., about 16,000). The results are shown in FIG. 1.

As is clear from the test results, for the samples from W3110/pIN5T4, 50% h-IFN-γ in the supernatant was decomposed within 15 minutes when left to stand and about 100% decomposition was exhibited when left to stand for 60 minutes. On the other hand, for samples from W3110(M25)/pIN5T4, no remarkable decomposition was seen even after being left to stand for 60 minutes, and h-IFN-γ having a molecular weight of about 18,000 was found to be present in a stable state. In addition, it was confirmed that there was no substantial difference in the yield of h-IFN-γ between the above two transformants. 4. Extraction and Purification of h-IFN-γ from the transformant derived using a mutated host strain:

W3110/pIN5T4 and W31110(M25)/pIN5T4 were separately cultured at 30° C. for 36 hours in 20 l of LB medium in a 30 l jar fermenter. In each case the resulting culture solution was centrifuged at 8,000 rpm for 10 minutes to collect cells. The wet cells (1 kg) were suspended in 7,000 ml of 20 mM Tris-HCl buffer (pH, 7.5), and disrupted with a homogenizer M15 (Manton Gaulin) at 8,000 psi. For W3110/pIN5T4, 20 mM Tris-HCl buffer containing 1 mM ZnCl$_2$ was used instead of the same buffer without ZnCl$_2$. The disrupted solution was centrifuged at 7,000 rpm for 20 minutes, and to the resulting supernatant was added 15% polyethyleneimine (adjusted its pH to 8.0 with HCl) in an amount sufficient to ensure that the final concentration was 0.75. The solution was stirred for 10 minutes, allowed to stand at 4° C. for 2 hours, and centrifuged at 7,000 rpm for 20 minutes to remove the resulting precipitate. The supernatant was treated in the manner described hereunder to purify h-IFN-γ.

The supernatant was subjected to a QAE Sephadex A-25 (manufactured by Pharmacia Co., Ltd.) column equilibrated with a 20 mM N-2-hydroxyethylpiperadine-N'-3-propane sulfonate buffer (EPPS buffer) of pH 8.6 to obtain the nonadsorbed fraction. The fraction obtained was then subjected to treatment in a CM Sepharose CL6B (manufactured by Pharmacia Co., Ltd.) column equilibrated with 20 mM THB of pH 7.4 containing 0.1% of 2-mercaptoethanol (abbreviated as "2-ME" hereinafter) and the active fraction absorbed on the column was eluted with a linear concentration gradient of 0 to 0.5 M NaCl to collect fractions which has a high interferon activity. The interferon activity was measured in accordance with the method described in Japanese Patent Public Disclosure No. 201995/1983. Ammonium sulfate was then added to the fraction so as to achieve a 50% saturation and salting-out was then carried out, followed by centrifugation at 7,000 rpm for 20 minutes to obtain the precipitates. The precipitates were dissolved in a 20 mM sodium phosphate buffer (abbreviated at "20 mM PBS" hereinafter) of pH 7.4 containing 0.3 M NaCl and 0.1% 2-ME and subjected to treatment in a Sephacryl S-200 (manufactured by Pharmacia Co., Ltd.) column equilibrated with the same buffer solution to obtain a final product having a purity of more than 99.

The final yields of h-IFN-γ produced from W3110/pIN5T4 and W3110(M25)/pIN5T4 were 5% and 12%, respectively.

As explained hereinbefore, according to this invention, desired protein can be isolated in a yield twice that of the conventional technique, although the amount of protein is expressed in the same yield. In addition, since the desired protein is not decomposed even after disruption of the cells in which the protein was expressed, there is no need to use a protease inhibitor or a protein denaturation agent and thus, the extraction and purification steps can be conducted simply and efficiently.

We claim:

1. A protease deficient mutant derived from Escherichia coli strain W3110, said mutant being designated W3110(M25):FERM BP-1097.

2. A mutant according to claim 1, transformed by a plasmid containing the human immune interferon gene or derivatives thereof.

3. The transformed mutant of claim 2 comprising W3110(M25)/pIN5T4.

4. A process for producing human immune interferon, said process comprising the steps of:
   (a) culturing Escherichia coli strain W3110(M25) transformed with a plasmid containing the human immune interfron gene or derivatives thereof, and
   (b) extracting and/or purifying the interferon therefrom.

5. A process according to claim 4, wherein said transformed strain comprises W3110(M25)/pIN5T4.

* * * * *